United States Patent [19]
Grubbs et al.

[11] Patent Number: 5,849,851
[45] Date of Patent: Dec. 15, 1998

[54] ROMP OF FUNCTIONALIZED CYCLIC OLEFINS USING RUTHENIUM AND OSMIUM CARBENE COMPLEXES

[75] Inventors: Robert H. Grubbs; Sonbinh T. Nguyen; Marc A. Hillmyer, all of Pasadena, Calif.

[73] Assignee: California Institute of Technology, Pasadena, Calif.

[21] Appl. No.: 969,969

[22] Filed: Nov. 13, 1997

Related U.S. Application Data

[60] Continuation of Ser. No. 550,679, Oct. 31, 1995, which is a division of Ser. No. 282,827, Jul. 29, 1994, which is a continuation-in-part of Ser. No. 106,292, Aug. 13, 1993, Pat. No. 5,342,909, which is a division of Ser. No. 863,606, Apr. 3, 1992, Pat. No. 5,312,940.

[51] Int. Cl.$^6$ ................ C08F 4/80; C08F 32/00
[52] U.S. Cl. ............... 526/93; 526/308; 526/309; 526/171; 526/283; 526/286; 526/291; 526/305
[58] Field of Search ................ 526/171, 308, 526/309, 283, 93

[56] References Cited

U.S. PATENT DOCUMENTS

| | | | |
|---|---|---|---|
| 4,883,851 | 11/1989 | Grubbs et al. | 526/268 |
| 4,945,135 | 7/1990 | Grubbs et al. | 525/334 |
| 4,945,144 | 7/1990 | Grubbs et al. | 526/268 |
| 5,198,511 | 3/1993 | Brown-Wensley et al. | 526/113 |
| 5,296,566 | 3/1994 | Brown-Wensley et al. | 526/171 |
| 5,312,940 | 5/1994 | Grubbs et al. | 526/136 |
| 5,342,909 | 8/1994 | Grubbs et al. | 526/171 |

OTHER PUBLICATIONS

Hawley's Condensed Chemical Dictionary, Eleventh Edition, Van Nostrand Reinhold, New york, 1987, pp. 613, 614, and 854.

Burrell et al., Synthesis and Reactions of Ru(=CH$_2$) Cl (No)$_2$, A Stable Terminal MethyleneComplex and the Crystal Structure of Ru (CH$_2$PPF$_2$)$_2$ (n$^2$-C$_2$F$_4$Cl (N)) (PPH$_3$), J. Chem. Soc., Dalton Trans., 1991, pp. 609–614.

Ivin, K.J. "Olefin Metathesis", 1983, Academic Press, pp. vii–x, 34–36.

McGrath et al., "Aqueous Ring–Opening Methathesis Polymerization of 7–Oxanorbornene Derivatives Using Ruthenium Catalysts", 1990, pp. 525–536.

Novak et al., "Catlytic Organometallic Chemistry in Water: The Aqueous Ring–Opening Methathesis Polymerization of 7–Oxanobornene Derivatives", 1988, JACS, vol. 110, pp. 7542–43g.

Novak et al., "The Ring Opening Methathesis Polymerization of 7–Oxanobicyclo [2.2.2.] hept–5–ene Derivatives: A New Acyclic Polymeric Ionophere", 1988, JACS, vol. 110, pp. 961–61.

Hillmyer et al., "The Aqueous Ring–Opening Methathesis Polymerization of exo–N–Methyl–7–oxabicyclo [2.2.1] hept–5–ene–2, 3–dicarbonximide" 1991, pp. 162–163–.

Carter et al., "Review of the Chemistry of Cyclopropane Compounds", Apr. 20, 1964, pp. 497–525.

Schmidbaur et al., "Ylide Chemistry: An Account of Structural, Conformational and Redox Investigations" 1983m pp. 167–170.

"Metathesis of Functionalized Olefin", J. of Molecules Catalysis, 15 (1982), pp. 35–45.

Collman et al., Radical Mechanism for the Decomposition of RuOEP (CH$_2$CH$_3$)$_2$ Determination of the Metal–Carbon Bond Dissociation Energy, J. Am. Soc. vol. 198, pp. 1332–133 (1986).

Bruce et al., "Cyclopentadienyl–Ruthenium and –osmium Chemistry. Some Reactions ofSubstituted Vinylidene Complexes," *J. Organometallic Chem.* 171:C5–C8 (1979).

M.H.L. Green et al., "Carbene Complexes of Iron, Molybdenum, and Ruthenium: A NewRoute to Metal–Carbene Derivatives," *J. Chem. Soc.* (A) 794–797 (1971).

H. Le Bozec et al., "A New Route to Vinylcarbene Metal Complexes in One Step from2–Propyn–1–ols and Arene Ruthenium (∥) Derivatives," *J. Chem. Soc.* Chem. Comm. 219–221 (1989).

Nguyen et al., "Ring–Opening Metathesis Polymerization (ROMP) of Norborene by a GroupVIII Carbene Complex in Protic Media," *J. Am. Chem. Soc.* 114: 3974–3975 (1992).

(List continued on next page.)

*Primary Examiner*—Mark Nagumo
*Attorney, Agent, or Firm*—Limbach & Limbach L.L.P.

[57] ABSTRACT

Disclosed are ruthenium and osmium carbene compounds which are stable in the presence of a variety of functional groups and which can be used to catalyze olefin metathesis reactions on unstrained cyclic and acyclic olefins. Specifically, the present invention relates to carbene compounds of the formula

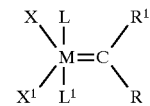

wherein: M is Os or Ru; R and R$^1$ are independently selected from hydrogen and functional groups C$_2$–C$_{20}$ alkenyl, C$_2$–C$_{20}$ alkynyl, C$_1$–C$_{20}$ alkyl, aryl, C$_1$–C$_{20}$ carboxylate, C$_2$–C$_{20}$ alkoxy, C$_2$–C$_{20}$ alkenyloxy, C$_2$–C$_{20}$ alkynyloxy, aryloxy, C$_2$–C$_{20}$ alkoxycarbonyl, C$_1$–C$_{20}$ alkylthio, C$_1$–C$_{20}$ alkylsulfonyl or C$_1$–C$_{20}$ alkylsulfinyl; each optionally substituted with C$_1$–C$_5$ alkyl, a halogen, C$_1$–C$_5$ alkoxy or with a phenyl group optionally substituted with a halogen, C$_1$–C$_5$ alkyl or C$_1$–C$_5$ alkoxy; X and X$^1$ are independently selected from any anionic ligand; and L and L$^1$ are each trialkyl phosphine ligands where at least one of the alkyl groups on the phosphine is a secondary alkyl or a cycloalkyl. A broad array of metathesis reactions are enabled including ring-opening metathesis polymerization of cyclic olefins, ring closing metathesis of acyclic dienes, cross metathesis involving at least one acyclic or unstrained cyclic olefin, and depolymerization of unsaturated polymers.

27 Claims, No Drawings

OTHER PUBLICATIONS

Grundy et al., "Migratory–Insertion Reactions of Osmium (II) Ethyl Complexes DerivedFrom an Osmium (0) Ethylene Complex," *J. Organometallic Chem.* 216:255–262 (1981).

Grundy et al., Propoinyl Complexes of Ruthenium Derived From the Reaction of Ethylenewith $RuHCl(CO)_2(PPh_3)_2$ *J. Organometallic Chem.* 265:77–85 (1984).

Richard R. Schrock, Living Ring–Opening Metathesis Polymerization Catalyzed by Well–Characterized Transition–Metal Alkylidene Complexes, Acc.Chem.Res. 1990, vol. 23, pp. 158–165.

Gregory C. Fu et al. "Catalytic Ring–Closing Metathesis of Functionalized Dienes by a Ruthenium Carbene Complex" Am. Chem Soc. 1993, pp. 9856–9867.

Robert H. Grubbs et al. Ring–Opening Metathesis Polymerization Catalysts Polymer Preprints 1994, 35(1), p. 688.

Marc A. Hillmyer et al. The ROMP of COD by a Well–Defined Metathesis Catalyst in the Presence of a Difunctional Chain Transfer Agent: The Preparation of Hydroxy–Telechlic 1,4–Poly (butadiene). Polymer Preprints 1993, 34(2), pp. 388–389.

Marc A. Hillmyer et al. "Preparation of Hydroxytelechelic Poly(butadiene) via Ring–Opening Metathesis Polymerization Employing a Well–Defined Metathesis Catalyst" Am. Chem. Soc. Macromolecules, vol. 26, No. 4, 1992, pp. 872–874.

SonBish R. Nguyen et al. "Syntheses and Activities of New Single–Component Ruthenium–Based Olefin Metathesis Catalysts" J. Am. Chem Soc. 1993, 115, 9858–9859.

ROMP OF FUNCTIONALIZED CYCLIC OLEFINS USING RUTHENIUM AND OSMIUM CARBENE COMPLEXES

This is a continuation of application Ser. No. 08/550,679 filed on Oct. 31, 1995, which is a divisional of application Ser. No. 08/282,827, filed Jul. 29, 1994, which is a continuation-in-part application of application Ser. No. 08/106,292 filed Aug. 13, 1993, now issued as U.S. Pat. No. 5,342,909, which is a divisional of application Ser. No. 07/863,606, filed Apr. 3, 1992 now issued as U.S. Pat. No. 5,312,940.

ORIGIN OF INVENTION

The U.S. Government has certain rights in this invention pursuant to Grant No. CHE-8922072 awarded by the National Science Foundation.

BACKGROUND OF THE INVENTION

This invention relates to highly active and stable ruthenium and osmium metal carbene complex compounds and their use as catalysts in olefin metathesis reactions.

During the past two decades, research efforts have enabled an in-depth understanding of the olefin metathesis reaction as catalyzed by early transition metal complexes. In contrast, the nature of the intermediates and the reaction mechanism for Group VIII transition metal catalysts has remained elusive. In particular, the oxidation states and ligation of the ruthenium and osmium metathesis intermediates are not known.

Many ruthenium and osmium metal carbenes have been reported in the literature (for example, see Burrell, A. K., Clark, G. R., Rickard, C. E. F., Roper, W. R., Wright, A. H., *J. Chem. Soc.*, Dalton Trans., 1991, Issue 1, pp. 609–614). However, the discrete ruthenium and osmium carbene complexes isolated to date do not exhibit metathesis activity to unstrained olefins. (Ivin, *Olefin Metathesis* pp. 34–36, Academic Press: London, 1983).

SUMMARY OF THE INVENTION

The present invention relates to ruthenium and osmium carbene compounds which are stable in the presence of a variety of functional groups and which can be used to catalyze olefin metathesis reactions on unstrained cyclic and acyclic olefins.

Specifically, the present invention relates to carbene compounds of the formula

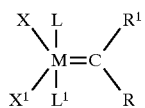

wherein:

M is Os or Ru;

R and $R^1$ are independently selected from hydrogen or a hydrocarbon selected from the group consisting of $C_2$–$C_{20}$ alkenyl, $C_2$–$C_{20}$ alkynyl, $C_1$–$C_{20}$ alkyl, aryl, $C_1$–$C_{20}$ carboxylate, $C_2$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl;

X and $X^1$ are independently selected from any anionic ligand; and

L and $L^1$ are each trialkyl phosphine ligands where at least one of the alkyl groups on the phosphine is a secondary alkyl or a cycloalkyl.

In a preferred embodiment, the hydrocarbon is selected from the group consisting of $C_1$–$C_5$ alkyl, halogen, $C_1$–$C_5$ alkoxy and a phenyl group.

In an alternative embodiment, the phenyl group is optionally substituted with halogen, $C_1$–$C_5$ alkyl and $C_1$–$C_5$ alkoxy.

In a preferred embodiment, all of the alkyl groups of the trialkyl phosphine are either a secondary alkyl or a cycloalkyl. In a more preferred embodiment, the alkyl groups are either isopropyl, isobutyl, sec-butyl, neopentyl, neophyl, cyclopentyl or cyclohexyl.

The present invention also relates to metathesis coupling of olefins catalyzed by the carbene compounds of the present invention. The high level metathesis activity of the ruthenium and osmium carbene compounds of the present invention enable these compounds to coordinate with and catalyze metathesis reactions between all types of olefins. By contrast, previous non-carbene ruthenium and osmium metathesis catalysts are only able to catalyze metathesis reactions involving highly strained olefins. As a result, a broad array of metathesis reactions are enabled using the carbene compounds of the present invention that cannot be performed using less reactive catalysts.

Examples of metathesis olefin coupling reactions enabled by the ruthenium and osmium carbene compounds of the present invention include, but are not limited to, ring-opening metathesis polymerization of strained and unstrained cyclic olefins, ring closing metathesis of acyclic dienes, cross metathesis reactions involving at least one acyclic or unstrained cyclic olefin and depolymerization of olefinic polymers.

DETAILED DESCRIPTION

The present invention relates to new highly active and stable ruthenium or osmium carbene compounds which can be used to catalyze olefin metathesis reactions.

Specifically, the present invention relates to carbene compounds of the formula

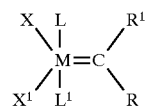

wherein:

M is Os or Ru;

R and $R^1$ are independently selected from hydrogen; $C_2$–$C_{20}$ alkenyl, $C_2$–$C_{20}$ alkynyl, $C_1$–$C_{20}$ alkyl, aryl, $C_1$–$C_{20}$ carboxylate, $C_2$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl or $C_1$–$C_{20}$ alkylsulfinyl; each optionally substituted with $C_1$–$C_5$ alkyl, halogen, $C_1$–$C_5$ alkoxy or with a phenyl group optionally substituted with halogen, $C_1$–$C_5$ alkyl or $C_1$–$C_5$ alkoxy;

X and $X^1$ are independently selected from any anionic ligand; and

L and $L^1$ are each trialkyl phosphine ligands where at least one of the alkyl groups on the phosphine is a secondary alkyl or a cycloalkyl.

In a preferred embodiment, all of the alkyl groups of the trialkyl phosphine are either a secondary alkyl or a cycloalkyl. In a more preferred embodiment, the alkyl groups are either isopropyl, isobutyl, sec-butyl, neopentyl, neophyl, cyclopentyl or cyclohexyl.

The high level metathesis activity of the carbene compounds of the present invention is observed when L and $L^1$ are alkyl phosphines where the carbon backbone of at least one alkyl group of the alkyl phosphine is a secondary alkyl or cycloalkyl. Substitution of the secondary alkyl and cycloalkyl with additional carbon moieties and/or other functional groups are intended to be included with the terms secondary alkyl and cycloalkyl.

The present invention also relates to metathesis coupling of olefins catalyzed by the carbene compounds of the present invention. The high level metathesis activity of the ruthenium and osmium carbene compounds of the present invention cause these compounds to coordinate with and catalyze metathesis reactions between all types of olefins. By contrast, previous non-carbene ruthenium and osmium metathesis catalysts are only able to catalyze metathesis reactions involving strained olefins. As a result, a broad array of metathesis reactions are enabled using the carbene compounds of the present invention that cannot be performed using less reactive catalysts.

Examples of reactions enabled by the ruthenium and osmium carbene compounds of the present invention include, but are not limited to, ring-opening metathesis polymerization of strained and unstrained cyclic olefins, ring closing metathesis of acyclic dienes, cross metathesis reactions involving at least one acyclic or unstrained cyclic olefin and depolymerization of olefinic polymers.

The carbene compounds disclosed in the present invention, as well as those disclosed in U.S. Pat. No. 5,312,940, are the only Ru and Os carbene complexes known to date in which the metal is formally in the +2 oxidation state (the carbene fragment is considered to be neutral), have an electron count of 16, and are pentacoordinate. Unlike most metathesis catalysts presently known which are poisoned by functional groups, the carbene compounds of the present invention are stable in the presence of a wide variety of functional groups including alcohol, thiol, ketone, aldehyde, ester, ether, amine, amide, nitro acid, carboxylic acid, disulfide, carbonate, carboalkoxy acid, isocyanate, carbodiimide, carboalkoxy, and halogen functional groups. As a result of their stability in the presence of functional groups, these catalysts may be employed in protic and aqueous solvents as well as mixtures of protic, aqueous, and/or organic solvents.

With regard to ligands R and $R^1$:

alkenyl can include vinyl, 1-propenyl, 2-propenyl; 3-propenyl and the different butenyl, pentenyl and hexenyl isomers, 1,3-hexadienyl and 2,4,6-heptatrienyl, and cycloalkenyl;

alkenyloxy can include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$;

alkoxy can include methoxy, ethoxy, n-propyloxy, isopropyloxy and the different butoxy, pentoxy and hexyloxy isomers;

cycloalkoxy can include cyclopentyloxy and cyclohexyloxy;

alkoxyalkyl can include $CH_3OCH_2$, $CH_3OCH_2CH_2$, $CH_3CH_2OCH_2$, $CH_3CH_2CH_2OCH_2$ and $CH_3CH_2OCH_2CH_2$; and alkoxycarbonyl can include $CH_3OC(\uparrow O)$; $CH_3CH_2OC(=O)$, $CH_3CH_2CH_2OC(=O)$, $(CH_3)_2CHOC(=O)$ and the different butoxy-, pentoxy- or hexyloxycarbonyl isomers;

alkyl can include methyl, ethyl, n-propyl, i-propyl, or the several butyl, pentyl or hexyl isomers and cycloalkyl isomers;

alkylsulfinyl can include $CH_3SO$, $CH_3CH_2SO$, $CH_3CH_2CH_2SO$, $(CH_3)_2CHSO$ and the different butylsulfinyl, pentylsulfinyl and hexylsulfinyl isomers;

alkylsulfonyl can include $CH_3SO_2$, $CH_3CH_2SO_2$, $CH_3CH_2CH_2SO_2$, $(CH_3)_2CHSO_2$ and the different butylsulfonyl, pentylsulfonyl and hexylsulfonyl isomers;

alkylthio can include, methylthio, ethylthio, and the several propylthio, butylthio, pentylthio and hexylthio isomers;

alkynyl can include ethynyl, I-propynyl, 3-propynyl and the several butynyl, pentynyl and hexynyl isomers, 2,7-octadiynyl and 2,5,8-decatriynyl;

alkynyloxy can include $HC\equiv CCH_2O$, $CH_3C\equiv CCH_2O$ and $CH_3C\equiv CCH_2OCH_2O$;

aryl can include phenyl, p-tolyl and p-fluorophenyl;

carboxylate can include $CH_3CO_2CH_3CH_2CO_2$, $C_6H_5CO_2$, $(C_6H_5) CH_2CO_2$;

cycloalkyl can include cyclopentenyl and cyclohexenyl.

diketonates can include acetylacetonate and 2,4-hexanedionate;

"halogen" or "halide", either alone or in compound words such as "haloalkyl", denotes fluorine, chlorine, bromine or iodine;

The anionic ligands X and $X^1$ may be any ligand which when removed from a metal center in its closed shell electron configuration has a negative charge. The critical feature of the carbene compounds of this invention is the presence of the ruthenium or osmium in the +2 oxidation state (the carbene fragment is considered to be neutral), an electron count of 16 and pentacoordination. A wide variety of anionic ligands, X and $X^1$ can be used where the carbene compound will still exhibit its catalytic activity.

With regard to the R, $R^1$, X and $X^1$ ligands, a preferred embodiment of the carbene compounds of the present invention is a compound where:

R and $R^1$ are independently selected from hydrogen, vinyl, $C_1-C_{10}$ alkyl, aryl, $C_1-C_{10}$ carboxylate, $C_2-C_{10}$ alkoxycarbonyl, $C_1-C_{10}$ alkoxy, aryloxy, each optionally substituted with $C_1-C_5$ alkyl, halogen, $C_1-C_5$ alkoxy or with a phenyl group optionally substituted with halogen, $C_1-C_5$ alkyl or $C_1-C_5$ alkoxy; and X and $X^1$ are independently selected from halogen, hydrogen, diketonates, or $C_1-C_{20}$ alkyl, aryl, $C_1-C_{20}$ alkoxide, aryloxide, $C_2-C_{20}$ alkoxycarbonyl, arylcarboxylate, $C_1-C_{20}$ carboxylate, aryl or $C_1-C_{20}$ alkylsulfonate, $C_1-C_{20}$ alkylthio, $C_1-C_{20}$ alkylsulfonyl, $C_1-C_{20}$ alkylsulfinyl, each optionally substituted with $C_1-C_5$ alkyl, halogen, $C_1-C_5$ alkoxy or with a phenyl group optionally substituted with halogen, $C_1-C_5$ alkyl or $C_1-C_5$ alkoxy.

In a further preferred embodiment,

R and $R^1$ are independently selected from hydrogen; vinyl, $C_1$–$C_5$ alkyl, phenyl, $C_2$–$C_5$ alkoxycarbonyl, $C_1$–$C_5$ carboxylate, $C_1$–$C_5$ alkoxy, phenoxy; each optionally substituted with $C_1$–$C_5$ alkyl, halogen, $C_1$–$C_5$ alkoxy or a phenyl group optionally substituted with halogen, $C_1$–$C_5$ alkyl or $C_1$–$C_5$ alkoxy; and X and $X^1$ are independently selected from Cl, Br, I, or benzoate, acetylacetonate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate; each optionally substituted with $C_1$–$C_5$ alkyl or a phenyl group optionally substituted with halogen, $C_1$–$C_5$ alkyl or $C_1$–$C_5$ alkoxy.

In a further preferred embodiment,

R and $R^1$ are independently vinyl, H, Me, Ph; and

X and $X^1$ are independently Cl, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate.

The most preferred carbene compounds of the present invention include:

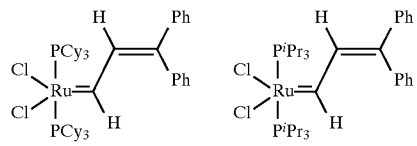

wherein $^i$Pr=isopropyl

Cy=cyclohexyl

The compounds of the present invention can be prepared by several different methods such as those taught in. The compounds of the present invention can be prepared by several different methods such as those taught in U.S. Pat. Nos. 5,312,940 and 5,342,909 which are incorporated by reference herein. A one step synthesis of the carbene compounds of the present invention is presented in Example 1.

The carbene complexes of the present invention have a well-defined ligand environment which enables flexibility in modifing and fine-tuning the activity level, stability, solubility and ease of recovery of these catalysts. The electron donating ability of the neutral electron donating ligands L and $L^1$ of the carbene complexes influences the activity of the catalyst. By using more electron donating alkyl substituents on the phosphines, one is able to conduct less energetically favored reactions, such as ROMP reactions on non-strained cycloalkenes and ring-closing metathesis reactions of acyclic dienes. By contrast, less reactive carbene catalysts, such as where L and $L^1$ are $P(Ph)_3$, are preferred in instances where selectivity of strained over unstrained alkenes is desired.

The solubility of the carbene compounds may be controlled by proper selection of either hydrophobic or hydrophilic ligands as is well known in the art. The desired solubility of the catalyst will largely be determined by the solubility of the reaction substrates and reaction products. It is well known in the art to design catalysts whose solubility is distinguishable from that of the reaction substrates and products, thereby facilitating the recovery of the catalyst from the reaction mixture.

The carbene compounds of the present invention, because of their higher level of metathesis activity, are able to catalyze the metathesis coupling of any two olefins. There are a very wide variety of reactions that are enabled by the ability of these carbene compounds to couple any two olefins.

For example, the carbene compounds of the present invention are useful as catalysts in the preparation of a wide variety of polymers which can be formed by the ring-opening metathesis polymerization of cyclic olefins. Unlike previous catalysts, the catalysts of the present invention are able to catalyze unstrained cyclic olefins such as cyclic olefins with a ring size of at least five atoms. One embodiment of this invention is an improved polymerization process comprising metathesis polymerization of a cyclic olefin by conducting the polymerization in the presence of a catalytic amount of a carbene compound of the present invention. The polymerization reaction is exemplified for 5-acetoxy-cyclooctene in the following equation:

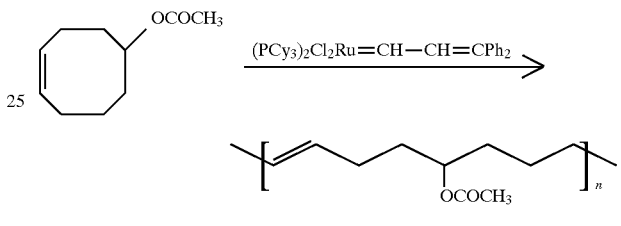

wherein n is the repeat unit of the polymeric chain.

Examples of cyclic olefins that may be used in this polymerization process include norbornene, cyclobutene, norbornadiene, cyclopentene, dicyclopentadiene, cycloheptene, cyclooctene, 7-oxanorbornene, 7-oxanorbornadiene, cyclooctadiene, cyclononene, cyclodecene, cyclononadiene, cyclopentadiene, and cyclododecene.

The polymerization reaction is generally carried out in an inert atmosphere by dissolving a catalytic amount of a carbene catalyst in a solvent and adding a cyclic olefin, optionally dissolved in a solvent, to the carbene solution. Preferably, the reaction is agitated (e.g., stirred). The progress of the reaction can be monitored by standard techniques, e.g., nuclear magnetic resonance spectroscopy.

Examples of solvents that may be used in the polymerization reaction include organic, protic, or aqueous solvents which are inert under the polymerization conditions, such as: aromatic hydrocarbons, chlorinated hydrocarbons, ethers, aliphatic hydrocarbons, alcohols, water, or mixtures thereof. Preferred solvents include benzene, toluene, p-xylene, methylene chloride, dichloroethane, dichlorobenzene, chlorobenzene, tetrahydrofuran, diethylether, pentane, methanol, ethanol, water, or mixtures thereof. More preferably, the solvent is benzene, toluene, p-xylene, methylene chloride, dichloroethane, dichlorobenzene, chlorobenzene, tetrahydrofuran, diethylether, pentane, methanol, ethanol, or mixtures thereof. Most preferably, the solvent is toluene or a mixture of benzene and methylene chloride. The solubility of the polymer formed in the polymerization reaction will depend on the choice of solvent and the molecular weight-of thepolymer obtained.

Under certain circumstances, no solvent is needed.

Reaction temperatures can range from 0° C. to 100° C., and are preferably 25° C. to 45° C. The ratio of catalyst to olefin is not critical, and can range from 1:5 to 1:30,000, preferably 1:10 to 1:6,000.

the new functionally substituted alkylidene reacts with a monomer to initiate a new chain. This process preserves the number of active catalyst centers and leads to symmetric telechelic polymers with a functionality that approaches 2.0.

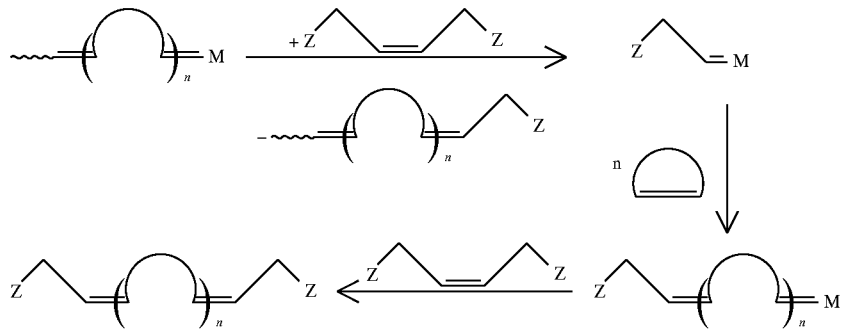

Because the carbene compounds mentioned above are stable in the presence of alcohol, thiol, ketone, aldehyde, ester, ether and halogen functional groups, these carbene compounds may be used to catalyze a wide variety of reaction substrates. The added stability also enables one to employ these catalysts in the presence of a protic solvents. This is very unusual among metathesis catalysts and provides a distinct advantage for the process of this invention over the processes of the prior art. Other advantages of the polymerization process of this invention derive from the fact that the carbene compounds are well-defined, stable Ru or Os carbene complexes providing high catalytic activity. Using such compounds as catalysts allows control of the rate of initiation, extent of initiation, and the amount of catalyst.

The high level metathesis activity of the carbene compounds also make these compounds useful for catalyzing the ring-closing metathesis of acyclic dienes as described in Fu, G., et al., *J. Am. Chem. Soc.*, 1993, 115:9856–9858 which is incorporated herein by reference.

The carbene compounds may also be used for the preparation of telechelic polymers. Telechelic polymers are macromolecules with one or more reactive end-groups. Telechelic polymers are useful materials for chain extension processes, block copolymer synthesis, reaction injection molding, and network formation. Uses for telechelic polymers and their synthesis is described in Goethals, *Telechelic Polymers: Synthesis and Applications* (CRC Press: Boca Raton, Fla., 1989).

For most applications, a highly functionalized polymer, i.e., a polymer where the number of functional groups per chain is 2 or greater, is required. Thus, it is desirable that the catalyst used to form the telechelic polymer be stable in the presence of functional groups.

The reaction scheme for a ROMP telechelic polymer synthesis is provided below. In a ROMP telechelic polymer synthesis, acyclic olefins act as chain-transfer agents to regulate the molecular weight of polymers produced. When α,ω-difunctional olefins are employed as chain-transfer agents, difunctional telechelic polymers can be synthesized. As shown in the reaction sequence, the chain-transfer reaction with a symmetric, α,ω-difunctional olefin, the propagating alkylidene is terminated with a functional group, and the new functionally substituted alkylidene reacts with a monomer to initiate a new chain. This process preserves the number of active catalyst centers and leads to symmetric telechelic polymers with a functionality that approaches 2.0.

The only polymer end-groups that do not contain residues from the chain-transfer agent are those from the initiating alkylidene and the end-capping reagent. In principle, these end-groups could be chosen to match the end-group from the chain-transfer agent.

Ring opening metathesis polymerization (ROMP) using $W(CHAr)(NPh)[OCCH_3(CF_3)_2]_2(THF)$ has been shown to be a viable polymerization technique for well-defined telechelic polymers. Hillmyer, et al., *Macromolecules*, 1993, 26:872. However, use of this carbene catalyst for telechelic polymer synthesis is limited by the instability of the tungsten catalyst in the presence of functional groups. The tungsten catalyst is also unstable in the presence of low concentrations of monomers.

The stability of the carbene compounds of the present invention to a wide range of functional groups as well as the ability of these carbene compounds to catalyze ROMP reactions make these compounds particularly desireable for the synthesis of telechelic polymers. The high level metathesis activity of the carbene compounds enable a wider range of cyclic and acyclic olefins to be employed. By way of example, the synthesis of hydroxytelechelic polybutadiene is described in Example 5.

The following examples set forth the synthesis and application of the ruthenium and osmium carbene compounds of the present invention. The following examples also set forth the preferred embodiments of the present invention. Further objectives and advantages of the present invention other than those set forth above will become apparent from the examples which are not intended to limit the scope of the present invention.

The abbreviations Me, Ph, $^i$Pr, Cy and THF used in the following examples refer to methyl, phenyl, isopropyl, cyclohexyl and tetrahydrofuran, respectively.

EXAMPLES

1. One Step Synthesis Of Carbene Compounds Of The Present Invention

The carbene compounds of the present invention may be prepared in a one step synthesis as illustrated in the reaction sequence below.

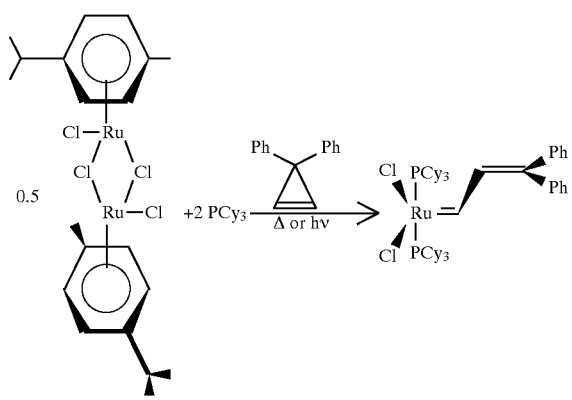

In a typical reaction, [(Cymene)RuCl$_2$]$_2$ dimer complex (0.53g, 1.73 mmol Ru) and PCy$_3$ (0.91 g, 2 equiv) were loaded under inert atmosphere into a 100 mL Sclenk flask equipped with a magnetic stirbar. Benzene (40 mL) was then added followed by 3,3-diphenylcyclopropene (0.33g, 1 equiv). The reaction flask was then attached to a reflux condenser under an inert atmosphere and heated in an oilbath at 83°–85° C. for 6 hours. The solvent was then removed to complete dryness in vacuo and the remaining red solid washed with pentane (4×25 mL) under inert atmosphere. The remaining red powder was dried under vacuum for 12 h and stored under an inert atmosphere yielding 1.4 g of Cl$_2$Ru(PCy$_3$)$_2$(=CCH=CPh$_2$) in 88% yield.

2. Effect Of Secondary Alkyl Substituents On Catalyst Turnover Rate

The activity of the carbene catalysts of the present invention have been found to be proportional to the number of secondary alkyl or cycloalkyl substituents on the phosphine. For example, in the reaction

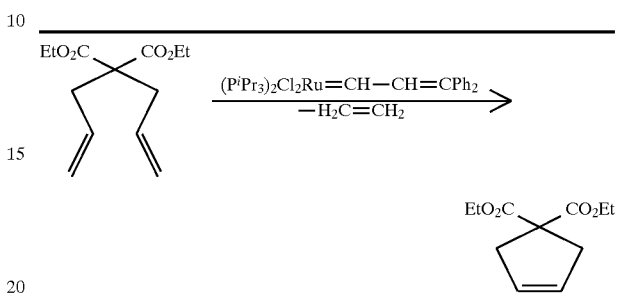

| PR$_3$ | Relative rate |
|---|---|
| P$^i$Pr$_3$ | 3.2 |
| P$^i$Pr$_2$Ph | 1.0 |
| P$^i$PrPh$_2$ | 0.0 | the turnover rate per hour of the catalyst increases as the number of isopropyl substituents on the phosphine increases.

TABLE 1

Catalytic Ring-Closing Metathesis of Dienes
(2–4 mol % [Ru], C$_6$H$_{69}$ 20° C.)

| entry | substrate | | product | time (hours) | yield (%) |
|---|---|---|---|---|---|
| 1 | X = CF$_3$ | | | 1 | 93 |
| 2 | Ot—Bu | | | 1 | 91 |
| 3 | | | | 1 | 89 |
| 4 | n = 0 | | | 22 | 78 |
| 5 | 1 | | | 6 | 93 |
| 6 | 2 | | | 40 | 81 |
| 7 | | | | 2 | 84 |

TABLE 1-continued

Catalytic Ring-Closing Metathesis of Dienes
(2–4 mol % [Ru], $C_6H_{60}$, 20° C.)

| entry | substrate | product | time (hours) | yield (%) |
|---|---|---|---|---|
| 8 | (allyl ether with OCHPh branch, terminal alkyne) | (dihydropyran with Ph) | 5 | 86 |
| 9 | (diene ether with Ph) | (7-membered oxacycle with Ph) | 8 | 72 |
| 10 | (bis-allyloxy acetal with Ph) | (cyclic acetal with Ph) | 1 | 87 |
| 11 | (diene with OTBS) | (cyclopentene with OTBS) | 2 | 85 |

3. Ring-Closing Metathesis Of Functionalized Dienes

Table 1 depicts the synthesis of several cycloalkenes from functionalized dienes using $Cl_2Ru(PCy_3)_2(=CCH=CPh_2)$ wherein Cy is cyclohexyl. A typical experimental protocol for performing ring-closing metathesis on the diene of entry 8 of Table 1 is as follows.

The diene of entry 8 (0.50 mmol) was added to a homogeneous orange-red solution of 0.01 mmol $Cl_2Ru(PCy_3)_2(=CCH=CPh_2)$ in 15 mL of dry benzene under argon. The resulting mixture was then stirred at 20° C. for 5 h, at which time thin layer chromatography showed the reaction to be complete. The reaction was then quenched by exposure to air (until greenish-black, 6 h), concentrated and purified by flash chromatography (0→6% $Et_2O$/hexane) to yield dihydropyran as a colorless oil in 86% yield.

4. Carbene Catalyzed Polymerization Of 5-Acetoxy-cyclooctene

The carbene eompounds of the present invention may be used in the polymerization of nonstrained cyclic olefins such as cyclooctene as depicted in the reaction sequence below.

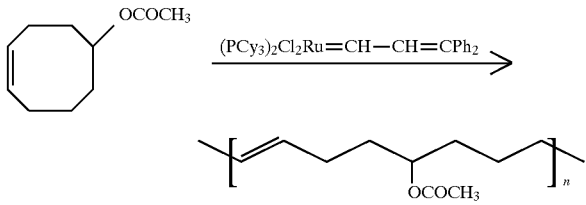

In order to polymerize 5-acetoxy-cyclooctene, a small vial was charged with 2.6 g of degassed 5-acetoxy-cyclooctene and a stirbar. A solution of 15 mg of $Cl_2Ru(PCy_3)_2(=CCH=CPh_2)$ in 200 μL of $CH_2Cl_2$ was added to the vial under inert atmosphere. The vial was capped and placed in an oil bath at about 48° C. After about 2.5 hours, the red-orange solution became noticeably viscous. After about 5.5 hours, the contents of the vial were solid. After 24 hours, the vial was removed from the oil bath and cooled to room temperature. The cap was removed from the vial and 100 μL of ethyl vinylether, 10 mL of chloroform and about 10 mg of 2,6-di-tert-butyl-4-methylphenol (butylated hydroxytoluene) were added to the vial to dissolve the solid, yielding a yellow-orange solution. After about 12 hours of stirring, an additional 20 mL of chloroform was added to the solution. The resulting solution was then poured into about 200 mL of methanol yielding an off-white precipitate. The off-white solid was stirred in the methanol until it appeared free of color. The resulting white solid was then isolated and dried under vacuum in 85% yield (2.2 g).

5. Synthesis of Hydroxytelechelic polybutadiene.

The carbene compounds may also be used to synthesize telechlic polymers such as hydroxytelechelic polybutadiene as described below. A one-neck, 500 mL, Schlenk flask, equipped with a magnetic stirbar, was charged with 1,5-cyclooctadiene (103.3 g, 955 mmol, 3673 equiv). Toluene (103.1 g) and 1,4-diacetoxy-cis-2-butene (11.4 g, 66.2 mmol, 255 equiv) were added to the reaction flask. A stopcock was placed in the neck of the flask and the reaction mixture was stirred, cooled to 0° C., and subjected to vacuum (~0.05 mm Hg) at 0° C. for 30 minutes. The reaction mixture was back-filled with argon, and with a continuous argon flow, $Cl_2Ru(PCy_3)_2(CHCHCPh_2)$ (0.245 g, 0.26 mmol, 1.0 equiv) was added as a solid to the reaction flask while stirring. The stopcock was replaced by a septum, and the system was subjected to vacuum (~0.05 mm Hg) at 0° C. for 10 minutes. The dark red-orange reaction mixture was placed in an oil bath at 45°–50° C. and stirred for 44 h under a slow purge of argon. The light orange reaction mixture was allowed to warm to room temperature. Vinyl acetate (14 g, 15 mL, 163 mmol, 627 equiv) and BHT (2,6-di-tert-butyl-4-methylphenol) (15 mg) were added to the reaction mixture under argon. The mixture was stirred at room temperature for 0.5 h, placed in an oil bath at 45°–50° C., and stirred for 7 h. The reaction mixture was allowed to cool to room temperature and poured into 800 mL of methanol. The mixture was stirred overnight and the polymer was isolated by centrifugation. The polymer was then redissolved in 400 mL tetrahydrofuran, cooled to 0° C. and 100 mL of 0.7M sodium methoxide in methanol (70 mmol sodium methoxide) was added at 0° C. The mixture was allowed to stir at 0° C. for 3.5 h. Methanol (400 mL) was then added to the reaction mixture to precipitate the polymer. The reaction mixture was allowed to warm to room temperature, stirred overnight, and isolated by centrifugation.

6. Metathesis Of Methyl Oleate

In a nitrogen-filled glove box, methyl oleate (3.2g, 2000 equiv) was added to a vial containing a solution of $Cl_2(PCy_3)_2Ru$=CH—CH=$CPh_2$ (5 mg in 0.1 mL $CH_2Cl_2$). The vial was then capped and stirred at room temperature for 4 days. As illustrated in the reaction sequence below, an equilibrium mixture of metathesis products was produced.

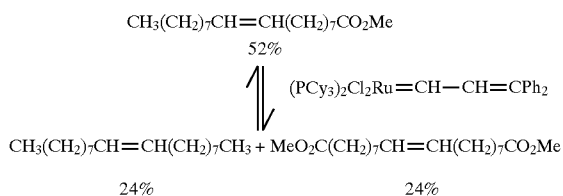

$$CH_3(CH_2)_7CH=CH(CH_2)_7CO_2Me$$
$$52\%$$
$$(PCy_3)_2Cl_2Ru=CH-CH=CPh_2$$
$$CH_3(CH_2)_7CH=CH(CH_2)_7CH_3 + MeO_2C(CH_2)_7CH=CH(CH_2)_7CO_2Me$$
$$24\% \qquad 24\%$$

7. Metathesis Of Oleic Acid

In a nitrogen-filled glove box, oleic acid (0.3g, 200 equiv) was added to a vial containing a solution of $Cl_2(PCy_3)_2Ru$=CH—CH=$CPh_2$ (5 mg in 0.1 mL $CH_2Cl_2$). The vial was then capped and stirred at room temperature for 4 days. As illustrated in the reaction sequence below, an equilibrium mixture of metathesis products was produced.

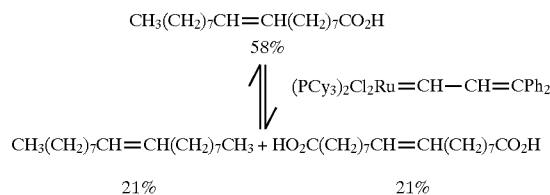

$$CH_3(CH_2)_7CH=CH(CH_2)_7CO_2H$$
$$58\%$$
$$(PCy_3)_2Cl_2Ru=CH-CH=CPh_2$$
$$CH_3(CH_2)_7CH=CH(CH_2)_7CH_3 + HO_2C(CH_2)_7CH=CH(CH_2)_7CO_2H$$
$$21\% \qquad 21\%$$

8. Metathesis of Methyl Oleate and Ethylene

In a nitrogen-filled glove box, methyl oleate (1 g, 152 equiv) was added to a Fisher-Porter tube containing a solution of $Cl_2(Cy_3)_2Ru$=CH—CH=$CPh_2$ (20 mg in 30 mL $CH_2Cl_2$). The tube was sealed, pressurized to 100 psi of ethylene, and then let stirred at room temperature for 12 hours. As illustrated in the reaction sequence below, an equilibrium mixture of metathesis products was produced.

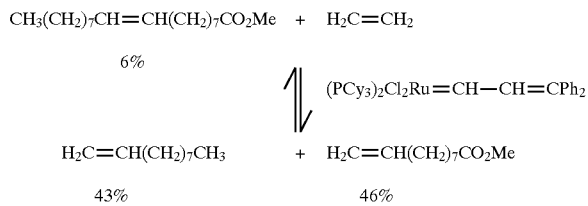

$$CH_3(CH_2)_7CH=CH(CH_2)_7CO_2Me + H_2C=CH_2$$
$$6\%$$
$$(PCy_3)_2Cl_2Ru=CH-CH=CPh_2$$
$$H_2C=CH(CH_2)_7CH_3 \qquad + \qquad H_2C=CH(CH_2)_7CO_2Me$$
$$43\% \qquad 46\%$$

-continued
$$CH_3(CH_2)_7CH=CH(CH_2)_7CH_3 + MeO_2C(CH_2)_7CH=CH(CH_2)_7CO_2Me$$
$$3\% \qquad 2\%$$

9. Metathesis of Oleic Acid and Ethylene

In a nitrogen-filled glove box, oleate acid (0.91 g, 300 equiv) was added to a Fisher-Porter tube containing a solution of $Cl_2(PCy_3)_2Ru$=CH—CH=$CPh_2$ (10 mg in 150 mL $CH_2Cl_2$). The tube was sealed, pressurized to 100 psi of ethylene, and then let stirred at room temperature for 12 hours. As illustrated in the reaction sequence below, an equilibrium mixture of metathesis products was produced.

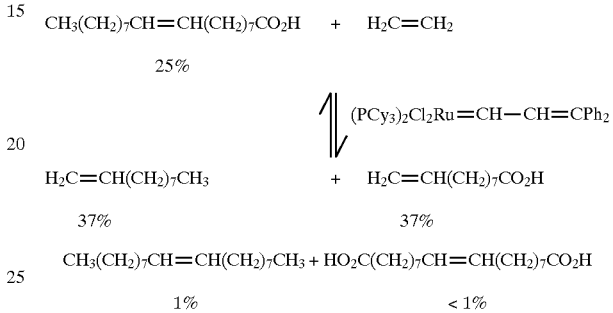

$$CH_3(CH_2)_7CH=CH(CH_2)_7CO_2H \qquad + \qquad H_2C=CH_2$$
$$25\%$$
$$(PCy_3)_2Cl_2Ru=CH-CH=CPh_2$$
$$H_2C=CH(CH_2)_7CH_3 \qquad + \qquad H_2C=CH(CH_2)_7CO_2H$$
$$37\% \qquad 37\%$$
$$CH_3(CH_2)_7CH=CH(CH_2)_7CH_3 + HO_2C(CH_2)_7CH=CH(CH_2)_7CO_2H$$
$$1\% \qquad <1\%$$

10. Depolymerization Of An Unsaturated Polymer With Ethylene

In a nitrogen-filled glove box, polyheptene (0.3 g) was added to a Fisher-Porter tube containing a solution of $Cl_2(PCy_3)_2Ru$=CH—CH=$CPh_2$ (20 mg in 5 mL $CH_2Cl_2$). The tube was sealed, pressurized to 60 psi of ethylene, and then let stirred at room temperature for 24 hours. As illustrated in the reaction sequence below, an equilibrium mixture of 1,8-nonadiene and its ADMET oligomers was produced.

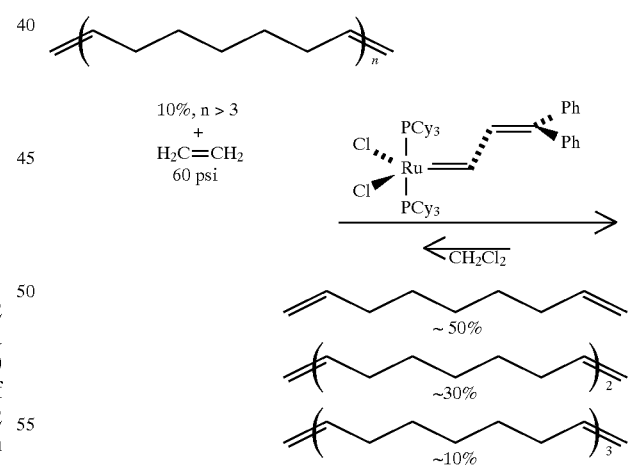

11. Synthesis of 1,6-Heptadiene From Cyclopentene

In a nitrogen-filled glove box, cyclopentene (1 g, 680 equiv) was added to a Fisher-Porter tube containing a solution of $Cl_2(PCy_3)_2Ru$=CH—CH=$CPh_2$ (20 mg in 5 mL $CCl_4$). The tube was sealed, pressurized to 60 psi of ethylene, and then let stirred at room temperature for 24 h. As illustrated in the reaction sequence below, an equilibrium mixture of 1,7-heptadiene and its ADMET oligomers was produced.

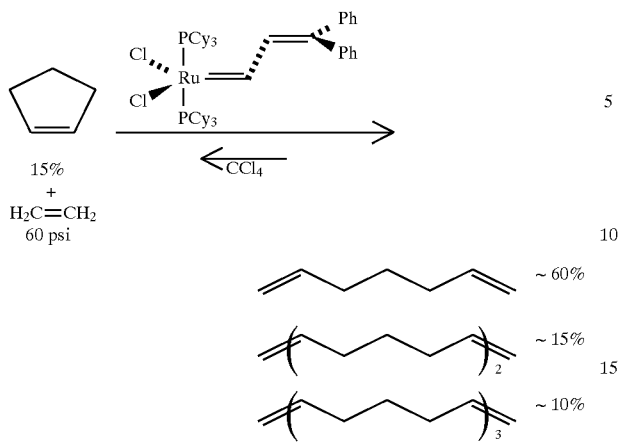

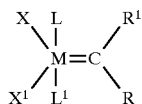

12. Ruthenium Carbene Catalyzed Polymerization of Dicyclopentadiene

A small Schlenk flask equipped with a small magnetic stir bar was charged with about 9.7 g of dicyclopentadiene (DCP) (Aldrich, 95%, inhibited with 200 ppm p-tert-butylcatechol (catalog #11,279-8)). The flask was stoppered with a greased ground glass stopper and placed in an oil bath at about 38° C. The DCP flask was subjected to vacuum (a reduced pressure of about 0.05 mmHg) and stirred for 30 minutes. Next, the flask was cooled to about 0° C. in an ice water bath for 5 minutes after which the DCP was solid. The flask was then back-filled with argon, the stopper was removed, and $(PCy_3)_2Cl_2Ru=CH—CH=CPh_2$ (20 mg) was added as a solid (no special precautions were taken to avoid atmospheric oxygen). The stopper was replaced, and the solids were subjected to vacuum for 10 minutes at about 0° C. The flask was placed in an oil bath at about 38° C. for 5 minutes while keeping its contents under vacuum. During this time the DCP liquefied, and the catalyst dissolved in the DCP to yield a non-viscous, red solution which appeared homogeneous. The stir bar was removed from the bottom of the flask with the aid of another magnet, and the temperature was raised to about 65° C. while keeping the contents of the flask under vacuum. When the temperature of the oil bath reached about 55° C. (about 2 minutes after the heating was initiated), the contents of the flask became yellow-orange and appeared to be solid. The temperature of the oil bath was maintained at about 65° C. for 1 hour. The flask was removed from the oil bath, back filled with air, broken, and the solid plug of polymer was removed. The polymer was washed with pentane and placed in an oven at about 130° C. for 3 hours. The polymer was removed from the oven, cooled to room temperature, and weighed (8.3 g, 86%, [DCP]/[Ru]~2900). (Losses due the removal of volatiles during the degassing were not taken into account in the calculation of the yield.)

While the present invention is disclosed by reference to the preferred embodiments and examples detailed above, it is to be understood that these examples are intended in an illustrative rather than limiting sense, as it is contemplated that many modifications within the scope and spirit of the invention will readily occur to those skilled in the art and the appended claims are intended to cover such variations.

What is claimed is:

1. A process for metathesis polymerization of a cyclic olefin, comprising contacting a functionalized or unfunctionalized cyclic olefin with a compound of the formula $$\begin{array}{c} X \quad L \quad R^1 \\ \diagdown \mid \diagup \\ M=C \\ \diagup \mid \diagdown \\ X^1 \quad L^1 \quad R \end{array}$$

wherein:

M is selected from the group consisting of Os and Ru;

R and $R^1$ are independently selected from the group consisting of hydrogen and a substituent group selected from the group consisting of $C_1$–$C_{20}$ alkyl, $C_2$–$C_{20}$ alkenyl, $C_2$–$C_{20}$ alkoxycarbonyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy and aryloxy; the substituent group optionally substituted with a moiety selected from the group consisting of $C_1$–$C_5$ alkyl, halogen, $C_1$–$C_5$ alkoxy, and phenyl; the phenyl optionally substituted with a moiety selected from the group consisting of halogen, $C_1$–$C_5$ alkyl, and $C_1$–$C_5$ alkoxy;

X and $X^1$ are independently selected from any anionic ligand; and

L and $L^1$ are independently selected from any phosphine of the formula $PR^3R^4R^5$, wherein $R^3$ is selected from the group consisting of neophyl, secondary alkyl and cycloalkyl and wherein $R^4$ and $R^5$ are independently selected from the group consisting of aryl, neophyl, $C_1$–$C_{10}$ primary alkyl, secondary alkyl, and cycloalkyl.

2. The process according to claim 1 wherein $R^3$, $R^4$ and $R^5$ are independently selected from the group consisting of neophyl, secondary alkyl and cycloalkyl.

3. The process according to claim 2, wherein $R^3$, $R^4$ and $R^5$ are independently selected from the group consisting of isopropyl, isobutyl, sec-butyl, neopentyl, neophyl, cyclopentyl and cyclohexyl.

4. The process according to claim 1 wherein L and $L^1$ are independently selected from the group consisting of P(isopropyl)$_3$, P(cyclopentyl)$_3$ and P(cyclohexyl)$_3$.

5. The process according to claim 1 wherein the functionalized cyclic olefin includes a functional moiety selected from the group consisting of alcohol, thiol, ketone, aldehyde, ester, disulfide, carbonate, imine, carboxyl, amine, amide, nitro acid, carboxylic acid, isocyanate, carbodiimide, ether and halogen.

6. The process according to claim 4 wherein the functional moiety is incorporated as part of a substituent of the cyclic olefin.

7. The process according to claim 4 wherein the functional moiety is incorporated as a part of a carbon chain of the cyclic olefin.

8. The process according to claim 1, wherein the contacting step is conducted without a solvent.

9. The process according to claim 1, wherein the contacting step is conducted in a solvent selected from the group consisting of protic solvent, aqueous solvent, organic solvent, and mixtures thereof.

10. The process according to claim 1 wherein, the functionalized or unfunctionalized cyclic olefin has a ring size of at least five atoms.

11. The process according to claim 1 wherein, the cyclic olefin is selected from the group consisting of cyclobutene, cycloheptene, cyclonocnene, cyclononene, cyclodecene, cyclooctadiene, cyclononadiene, cyclopentadiene, and dicyclopentadiene.

12. A process for metathesis polymerization of a functionalized cyclic olefin comprising, contacting a functionalized cyclic olefin with a compound of the formula

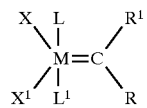

wherein:
the functionalized cyclic olefin includes a moiety selected from the group consisting of alcohol, thiol, ketone, aldehyde, ester, ether, amine, amide, nitro acid, carboxylic acid, disulfide, carbonate, carboalkoxy acid, isocyanate, carbodiimide, carboalkoxy, and halogen;

M is selected from the group consisting of Os and Ru;

R and $R^1$ are independently selected from the group consisting of hydrogen and a first substituent group selected from the group consisting of vinyl, $C_1$–$C_{10}$ alkyl, aryl, $C_1$–$C_{10}$ carboxylate, $C_2$–$C_{10}$ alkoxycarbonyl, $C_1$–$C_{10}$ alkoxy, and aryloxy; the first substituent group optionally substituted with a group selected from the group consisting of $C_1$–$C_5$ alkyl, halogen, $C_1$–$C_5$ alkoxy, and phenyl; the phenyl optionally substituted with a group selected from the group consisting of halogen, $C_1$–$C_5$ alkyl, and $C_1$–$C_5$ alkoxy;

X and $X^1$ are independently selected from the group consisting of halogen, hydrogen, diketonates, and a second substituent group selected from the group consisting of $C_1$–$C_{20}$ alkyl, aryl, $C_1$–$C_{20}$ alkoxide, aryloxide, $C_2$–$C_{20}$ alkoxycarbonyl, arylcarboxylate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl; the secend substituent group optionally substituted with a group selected from the group consisting of $C_1$–$C_5$ alkyl, halogen, $C_1$–$C_5$ alkoxy, and phenyl; the phenyl optionally substituted with a group selected from the group consisting of halogen, $C_1$–$C_6$ alkyl, and $C_1$–$C_5$ alkoxy; and, L and $L^1$ are independently selected from any phosphine of the formula $PR^3R^4R^5$, wherein $R^3$, is selected from the group consisting of neophyl, secondary alkyl and cycloalkyl and wherein $R^4$, and $R^5$ are selected from the group consisting of aryl, neophyl, $C_1$–$C_{10}$ primary alkyl, secondary alkyl, and cycloalkyl.

13. The process according to claim 12, wherein:
R and $R^1$ are independently selected from the group consisting of hydrogen and a first substituent group selected from the group consisting of vinyl, $C_1$–$C_5$ alkyl, phenyl, $C_2$–$C_5$ alkoxycarbonyl, $C_1$–$C_5$ carboxylate, $C_1$–$C_5$ alkoxy, and phenoxy; the first substituent group optionally substituted with a group selected from the group consisting of $C_1$–$C_5$ alkyl, halogen, $C_1$–$C_5$ alkoxy and phenyl; the phenyl optionally substituted with a group selected from the group consisting of halogen, $C_1$–$C_5$ alkyl or $C_1$–$C_5$ alkoxy; and X and $X^1$ are independently selected from the group consisting of Cl, Br, I, and a second substituent group selected from the group consisting of benzoate, acetylacetonate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate; the second stibstituent group optionally substituted with a group selected from the group consisting of halogen, $C_1$–$C_5$ alkyl and phenyl; the phenyl optionally substituted with a group selected from the group consisting of halogen, $C_1$–$C_5$ alkyl, and $C_1$–$C_5$ alkoxy.

14. The process according to claim 13, wherein:
R and $R^1$ are independently selected from the group consisting ot vinyl, H, Me, and Ph; and X and $X^1$ are independently selected from the group consisting of Cl, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

15. The process according to claim 12, wherein $R^3$, $R^4$, and $R^5$ are independently selected from the group consisting of neophyl, secondary alkyl and cycloalkyl.

16. The process according to claim 15, wherein $R^3$, $R^4$, and $R^5$ are independently selected from the group consisting of isopropyl, isobutyl, sec-butyl, neopentyl, neophyl, cyclopentyl and cyclohexyl.

17. The process according to claim 12, wherein L and $L^1$ are independently selected from the group consisting of P(isoprepyl)$_3$, P(cyclopentyl)$_3$ and P(cyclohexyl)$_3$.

18. The process according to claim 12, wherein the functionalized cyclic olefin has a ring size of at least five atoms.

19. The process according to claim 12, wherein the functionalized cyclic olefin is selected from the group consisting of cyclobutene, cycloheptene, cyclooctene, cyclononene, cyclodecene, cyclooctadiene, cyclononadiene, cyclopentadiene, and dicyclopentadiene.

20. The process according to claim 12, wherein the process is conducted without a solvent.

21. The process according to claim 12, wherein the process is conducted in a solvent selected from the group consisting of protic solvent, aqueous solvent, organic solvent, and mixtures thereof.

22. A process for metathesis polymerization of a fulnctionalized cyclic olefin comprising, contacting a furictionalized cyclic olefin with a compound selected from the group consisting of

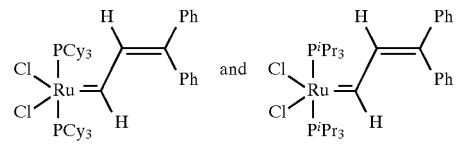

wherein Cy is cyclopentyl or cyclohexyl and $^iPr$ is isopropyl.

23. The process according to claim 22, wherein the functionalized cyclic olefin contains a moiety selected from the group consisting of alcohol, thiol, ketone, aldehyde, ester, disulfide, carbonate, imine, carboxyl, amine, amide, nitro acid, carboxylic acid, isocyanate, carbodiimide, ether, and halogen.

24. The process according to claim 22, wherein the contacting step is conducted without a solvent.

25. The process according to claim 22, wherein the contacting step is conducted in a solvent selected from the group consisting of protic solvent, aqueous solvent, organic solvent, and mixtures thereof.

26. The process according to claim 22, wherein the functionalized cyclic olefin has a ring size of at least five atoms.

27. The process according to claim 22, wherein the functionalized cyclic olefin is selected from the group consisting of cyclobutene, cycloheptene, cyclooctene, cyclononene, cyclodecene, cyclooctadiene, cyclononadiene, cyclopentadiene, and dicyclopentadiene.

* * * * *